United States Patent
Yeung et al.

(10) Patent No.: US 10,155,060 B2
(45) Date of Patent: Dec. 18, 2018

(54) INORGANIC GEL FOR CONTROLLED RELEASING OF FRAGRANCE AND DISINFECTANT

(75) Inventors: King Lun Yeung, Hong Kong (CN); Wei Han, Hong Kong (CN); Shengli Cao, Hong Kong (CN); Wai Kwong Ching, Hong Kong (CN)

(73) Assignee: THE HONG KONG UNIVERSITY OF SCIENCE AND TECHNOLOGY, Kowloon, Hong Kong (CN)

( * ) Notice: Subject to any disclaimer, the term of this patent is extended or adjusted under 35 U.S.C. 154(b) by 113 days.

(21) Appl. No.: 13/997,795

(22) PCT Filed: Dec. 21, 2011

(86) PCT No.: PCT/CN2011/002153
§ 371 (c)(1),
(2), (4) Date: Jun. 25, 2013

(87) PCT Pub. No.: WO2012/088758
PCT Pub. Date: Jul. 5, 2012

(65) Prior Publication Data
US 2013/0287723 A1    Oct. 31, 2013

Related U.S. Application Data

(60) Provisional application No. 61/457,095, filed on Dec. 27, 2010.

(51) Int. Cl.
| | |
|---|---|
| *A61L 9/012* | (2006.01) |
| *A01N 65/00* | (2009.01) |
| *A01N 25/00* | (2006.01) |
| *A61L 9/04* | (2006.01) |
| *A01N 25/04* | (2006.01) |
| *A01N 65/28* | (2009.01) |
| *A01N 65/36* | (2009.01) |
| *A01N 65/48* | (2009.01) |

(52) U.S. Cl.
CPC .............. *A61L 9/048* (2013.01); *A01N 25/04* (2013.01); *A01N 65/00* (2013.01); *A01N 65/28* (2013.01); *A01N 65/36* (2013.01); *A01N 65/48* (2013.01); *A61L 9/012* (2013.01)

(58) Field of Classification Search
CPC ........ A01N 25/04; A01N 65/28; A01N 65/36; A01N 25/18; A01N 59/00; A01N 65/06; A01N 65/00; A01N 65/48; A61L 9/012; A61L 9/048
See application file for complete search history.

(56) References Cited

U.S. PATENT DOCUMENTS

| | | | |
|---|---|---|---|
| 4,717,544 A | 1/1988 | Calcaterra et al. | |
| 4,883,828 A | 11/1989 | Oakes et al. | |
| 4,927,750 A | 5/1990 | Dorn | |
| 5,244,667 A | 9/1993 | Hagiwara et al. | |
| 5,264,197 A * | 11/1993 | Wang et al. | 423/338 |
| 5,616,347 A * | 4/1997 | Alliger et al. | 424/665 |
| 5,637,401 A * | 6/1997 | Berman et al. | 516/111 |
| 5,658,573 A * | 8/1997 | Holcomb | 424/400 |
| 5,750,498 A | 5/1998 | Soeda et al. | |
| 5,830,480 A * | 11/1998 | Ducheyne et al. | 424/400 |
| 5,914,120 A * | 6/1999 | Wellinghoff et al. | 424/406 |
| 6,015,843 A | 1/2000 | Van Vlasselaer et al. | |
| 6,046,243 A * | 4/2000 | Wellinghoff et al. | 514/772.3 |
| 6,071,506 A | 6/2000 | Semoff et al. | |
| 6,689,341 B2 * | 2/2004 | Galli | 424/49 |
| 7,235,261 B2 | 6/2007 | Smith et al. | |
| 2002/0039566 A1 | 4/2002 | Triplett et al. | |
| 2003/0152528 A1 * | 8/2003 | Singh et al. | 424/53 |
| 2005/0037080 A1 | 2/2005 | Lynch et al. | |
| 2005/0226900 A1 * | 10/2005 | Winton Brooks et al. | 424/401 |
| 2005/0271595 A1 * | 12/2005 | Brown | 424/10.1 |
| 2005/0274817 A1 | 12/2005 | Maat | |
| 2006/0094629 A1 | 5/2006 | Horton, III | |
| 2010/0136657 A1 * | 6/2010 | Jokinen et al. | 435/235.1 |
| 2010/0143422 A1 * | 6/2010 | Popplewell et al. | 424/401 |
| 2013/0101633 A1 | 4/2013 | Lowenhielm et al. | |

FOREIGN PATENT DOCUMENTS

| | | |
|---|---|---|
| CN | 1263709 A | 8/2000 |
| CN | 1263709 C | 7/2006 |
| CN | 1970150 A | 5/2007 |
| EP | 1 415 646 B1 | 5/2004 |
| EP | 2 460 409 A1 | 6/2012 |
| JP | 2005-194308 A | 7/2005 |

OTHER PUBLICATIONS

Veith et al., Encapsulation and retention of decanoic acid in sol-gel-made silicas. Journal of Colloid and Interface Science 283 (2005) 495-502.*

(Continued)

*Primary Examiner* — Robert A Wax
*Assistant Examiner* — Olga V Tcherkasskaya
(74) *Attorney, Agent, or Firm* — Nath, Goldberg & Meyer; Joshua B. Goldberg; Scott H. Blackman

(57) ABSTRACT

A gel composition for air freshening or disinfecting, comprising a silicon alkoxide or colloidal silica, a volatile or gaseous fragrance and/or disinfectant, water, an acid or base catalyst, a water-soluble solvent, and optionally other volatile components and additives, and a method for preparing the same. The gel can be transparent or colored, has a homogeneous texture and a soft to rigid structure, and contains volatile or gaseous components from 0 vol % to 85 vol % for scented materials (fragrance and oils) and/or 0-8000 ppm of disinfectant, which are released at a steady rate under ambient conditions, controlled by the shape and opening of the gel container. Botanicals or plastic decorations may be added into the gel to improve its aesthetic appeal. The preparation method is easier and requires less energy consumption and the gel is used as an air freshener or disinfectant.

12 Claims, 18 Drawing Sheets

(56) References Cited

OTHER PUBLICATIONS

Pyankov, O.V., et al.,"Removal of Biological Aerosols by Oil Coated Filters", www.clean-journal.com, Clean 36(7), pp. 609-614, (2008).

Ziani, K., et al., "Influence of Surfactant Charge on Antimicrobial Efficacy of Surfactant-Stabilized Thyme Oil Nanoemulsions", Journal of Agricultural and Food Chemistry, 59, pp. 6247-6255, (2011).

Viyoch, J., et al.,"Evaluation of in vitro antimicrobial activity of Thai basil oils and their micro-emulsion formulas against Propionibacterium acnes", International Journal of Cosmetic Science, 28, pp. 125-133, (2006).

Huang, R., et al., "Inactivation of Fungal Spores Collected on Fibrous Filters by *Melaleuca alternifolia* (Tea Tree Oil)", Aerosol Science and Technology, 44:4, pp. 262-268, (2010).

Si, W., et al., "In vitro assessment of antimicrobial activity of carvacrol, thymol and cinnamaldehyde towards *Salmonella* serotype Typhimurium DT104: effects of pig diets and emulsification in hydrocolloids", Journal of Applied Microbiology, 101 pp. 1282-1291, (2006).

* cited by examiner

INORGANIC GEL FOR CONTROLLED RELEASING OF FRAGRANCE AND DISINFECTANT

This is a National Phase Application filed under 35 U.S.C. 371 as a national stage of PCT/CN2011/002153, filed Dec. 21, 2011, an application claiming the benefit under 35 USC 119(e) U.S. from Provisional Patent Application No. 61/457,095, filed Dec. 27, 2010, the content of each of which is hereby incorporated by reference in its entirety.

FIELD OF THE INVENTION

The present subject matter relates to a composition suitable for use in air freshening or disinfecting gel-like or gel products, and a method of preparing the same. In particular, the present subject matter relates to a gel composition for air freshening or disinfecting, comprising an inorganic silica gel matrix for controlled releasing of a fragrance or disinfectant contained therein.

BACKGROUND OF THE INVENTION

Air fresheners are products capable of imparting a desired scent, e.g., fragrance, perfume or deodorant, into the air to give pleasant smells or mask offensive odors. They are often used in a closed area, such as, the interior of an automobile or household. In the household, they are mostly used for the area where unpleasant odors are likely to occur, such as bathrooms, kitchens, bedrooms, living rooms and the like.

Air fresheners have at times been prepared in the form of a paste or gel to control spills or leaks. Most of the air freshener gels commercially available in the market are aqueous-based gels in which colloidal dispersions of droplets of fragrance, such as volatile oily components, are distributed in a hydrocolloid matrix. The main components of such commercially available aqueous gels can often include a fragrance, a surfactant and a co-solvent. The aqueous gel is typically composed of water, a gelling agent and a cross-linking agent, and included in the air freshener gel in an amount of over 80 wt %, or more typically, over 90 wt %. See, for example, US Patent Application Publication No. 2005/0037080. The gelling agent typically includes carageenan, alginate, carboxymethylcellulose (CMC), gelatin or gellan glum. In practical effect, the cross-linking agent can interact with the gelling agent to from a matrix, which immobilizes the largely aqueous medium.

Typical fragrances present in the current products include complex mixtures of fragrant compounds with varying volatility. They are typically included in the air freshener gel in an amount of about 1 to 10 wt %. See, U.S. Patent Application Publication No. 2005/0037080. Top notes, the most volatile part of the fragrance, are often associated with the freshness and the first impression perceived by the customers. Middle notes and bottom notes, which are less volatile components, contribute to the long-lasting scents throughout the gel life time. Thus, the relatively steady emission of the fragrance during the period of use is an important issue for fragrance gels.

With the addition of the surfactant, the oily fragrance is emulsified into tiny droplets. Generally, nonionic surfactants are preferred as they can provide good activity and good gel clarity. Examples for the nonionic surfactants include ethoxylated alkyl phenol, nonyl phenols, ethyoxylated alcohols, and the like. See, U.S. Pat. No. 6,071,506. The clarity is related to the amounts of fragrance and surfactant in the gel composition.

Opaque or cloudy appearance of the gel results from phase separation due to an insufficient emulsification, which makes the gel undesirable for decorative purposes. The phase separation gets more serious and difficult to solve with high fragrance loadings. It may be possible to increase the concentration of the surfactant to reduce or eliminate the phase separation, but this may adversely affect the fragrance-dispersing capability. Moreover, a certain combination of the fragrance and surfactant may bring about clouding of the gel at lower temperatures due to breakdown of the oil-water microemulsion. See, U.S. Pat. No. 6,071,506. Relatively low fragrance loading brings an obvious disadvantage that a large amount of gel is required to provide sufficient scent to the ambient atmosphere. Thus, in the commercially available products, the package of the gel is usually between 50 g and 250 g, mostly between 100 g and 200 g. See, U.S. Patent Application Publication No. 2005/0274817.

The co-solvent used in such commercially available gels is typically a water-soluble compound to enhance the diffusion of the fragrance in the gel matrix, adjust the delivery rate of the fragrance into the surrounding air and improve the consistency of the fragrance release throughout the product lifetime. Co-solvents used most often include, for example, dipropylene glycol, propylene glycol, other glycol ethers, isopropylmyristate, diethyl phthalate, benzyl alcohol, benzyl benzoate, glyceryl triacetate, ethanol, isopropanol, and the like.

Many of the gel compositions and the preparation methods thereof used in the art involve problems in, for example, i) clarity, i.e., opaque or cloudy appearance due to phase separation of the aqueous-based components and the oily fragrance components; ii) fragrance loading, typically with a low loading of 1 to 10 wt % in the gel composition; iii) gel strength, i.e., soft gel texture relating to the interaction of fragrance, surfactant, co-solvent and cross-linking agents; iv) emission, i.e., consistent diffusing into the surrounding air without perceivable diminution; v) heating, typically at 50 to 80° C. to promote the dispersion, which increases the loss due to evaporation in the processing and greater energy consumption; vi) material cost, i.e., expensive gelling agents, cross-linking agents, and surfactants make the manufacturing less economical; and vii) complexity, i.e., the gel comprises many components interacting with each other to make the gel properties more versatile to control.

Several attempts have been made to solve one or more of these problems with air freshener gel preparation and properties. One such attempt resulted in a transparent gel, which is preferred by customers due to its aesthetic appeal. U.S. Pat. No. 5,750,498 teaches a preparation method for a transparent gelatin gel. The gel is prepared with gelatin obtained from bovine bone, bovine hide, pigskin or the like material. The protein in the gelatin is subject to cross-linking by addition of transglutaminase and the like. U.S. Pat. No. 6,071,506 provides another transparent gel composition prepared with a modified polysaccharide gelling agent and cationic cross-linking agent, such as potassium citrate. U.S. Patent Application Publication No. 2002/0039566 describes a preparation method of transparent gels, using a modified polysaccharide gelling agent without cross-linking or chelating agents. However, these transparent aqueous-based gels can incorporate the fragrance only in the amount of about 1 to 15 wt %, preferably less than 10 wt %. In addition, it is required to heat the gel composition to the temperature of 50 to 80° C. for an effective emulsification of the fragrance and the additional oily components.

Dispersion of the fragrance in the gel matrix can be effectively enhanced using anhydrous gels so that higher fragrance loading can be achieved. For example, U.S. Patent Application Publication No. 2005/0274817 describes an anhydrous gel comprising from 3 to 80 wt % of perfume base. To obtain the perfume base, perfume is mixed with cellulose esters, such as, cellulose acetate esters, cellulose acetate propionate and cellulose acetate butyrate. The gel is formed by vigorous stirring of the mixture at 60 to 100° C. and subsequent cooling of the resultant transparent viscous liquid. However, a careful selection of cellulose esters and a control of component concentrations are necessary therein to obtain transparent to slightly cloudy gels. Otherwise, either the esters are not well dispersed in the fragrance bases or the liquid mixture is not solidified upon cooling.

U.S. Patent Application Publication No. 2005/0037080 describes a method to prepare an aqueous-based gel without heating the mixture for fragrance dispersion and gelation. A gel-forming polymer, an added polymer, a gelling agent, a fragrance, a surfactant and water are premixed and preferably stirred at high speed to disperse the fragrance into the aqueous medium. Then, a pH modifier, such as glucono delta lactone, is added into the mixture to induce the linking of the gel-forming polymer to produce the gel. However, the gel contains only about 0.5 to 10 wt % of the fragrance, and the clarity is reported to be moderate to good.

Disinfectants are frequently used in hospitals, dental surgeries, kitchens, and bathrooms to kill infectious organisms. Gas disinfectants, such as sulfur dioxide, glyoxal, iodine, chlorine, malondialdehyde and ammonia, are well-known due to their high efficiency and simple utilization compared to liquid disinfectants. U.S. Pat. No. 4,717,544 uses thermally depolymerizing, solid polymeric aldehydes in this regard. Polyglutaraldehyde can slowly release gas monomers acting as a disinfectant. U.S. Pat. No. 4,883,828 describes adherent and water-resistant polymeric films prepared from liquid disinfectant compositions, which show prolonged germicidal properties of treated surfaces. US Patent Application Publication No. 2006/0094629 describes a cleaning composition comprising a disinfectant, a surfactant and a solvent. However, it is a great challenge to develop an effective and economical method for controlled release of the safe gas disinfectant.

Silicon alkoxide, when reacted with water, is hydrolyzed into silicon hydroxide, which with further reaction with each other and/or unhydrolyzed silicon alkoxide, can form a 3-dimensional silica network in the liquid medium. In addition, colloidal silica suspension can form a 3-dimensional gel framework by condensation. However, application of such an inorganic silica gel or colloidal silica suspension has not been attempted in the prior art in air fresheners or disinfectors.

SUMMARY OF THE INVENTION

The presently subject matter relates to a composition for air freshening or disinfecting gels and a method for preparing the same. The gel formed from the composition delivers volatile materials, such as fragrance oils, fragrance solutions, gaseous disinfectants, deodorants, insecticides and the like, into the surrounding air, without one or more of the problems in the prior art, as described above.

Accordingly, in one aspect, the present subject matter provides a gel composition for air freshening or disinfecting, comprising a silicon alkoxide or colloidal silica; a volatile fragrance and/or a gaseous disinfectant; water and/or an aqueous solution; a water-soluble solvent; and optionally, other volatile components and/or additives. The aqueous solution can comprise acid or base catalysts.

In one embodiment, the gel composition comprises the silicon alkoxide or colloidal silica in an amount of about 5 to 50 vol %, the fragrance and other volatile components in an amount of about 0 to 85 vol %, the gaseous disinfectant in an amount of about 0 to 8000 ppm and the water or aqueous solution in an amount of 1 to 50 vol %. In all cases, the gel composition comprises at least one of the volatile fragrance and the gaseous disinfectant.

In another embodiment, the gel composition comprises the silicon alkoxide or colloidal silica, volatile or gaseous fragrance and/or disinfectant and other volatile components, aqueous solution and water-soluble solvent being homogeneously mixed. The gel may be transparent and has a uniform and continuous texture without visible inhomogeneity caused by solid particles, oily droplets or air bubbles. The gel may have a soft to rigid framework.

In yet another embodiment, the gel composition releases the fragrance and/or disinfectant in a relatively stable way over several months and imparts a perceivable scent and/or disinfectant to the surrounding environment. The gel composition may contain botanicals or plastic decorations suspended therein, creating aesthetic attraction.

The present subject matter, in another aspect, provides a simple method for preparing a gel composition for air freshening, comprising forming a silica sol solution, adding a water-soluble solvent(s) to the silica sol solution to form a homogenous mixture, adding a fragrance and other volatile components to form a homogeneous mixture, adding a base aqueous solution to form a fragrance solution, transferring the resulting fragrance solution to a transparent container, and adding a botanical or plastic decoration into the fragrance solution in the container.

In yet another aspect, the present subject matter provides a method for preparing a disinfectant gel, comprising forming a colloidal silica suspension, dissolving reactants into the colloidal silica suspension by adding salts and acids to generate gaseous disinfectant by chemical and electrochemical reactions, transferring the suspension to a transparent container, and optionally adding a botanical or plastic decoration into the fragrance solution in the container.

BRIEF DESCRIPTION OF DRAWINGS

Various embodiments will now be described in detail with reference to the accompanying drawings.

FIG. 9(a) shows Eoil gel of Sample M, FIG. 9(b) shows Eoil gel of Sample M, FIG. 9(c) shows Eoil gel of Sample S (Left) and Sample R (Right) containing acid green, and FIG. 9(D) shows large-scaled gel of Sample V containing food pigment.

FIG. 14(a) shows those gels exposed in the air at room temperature for 3 h and 2 h. FIG. 14(b) shows those gels exposed in the air at room temperature for 15.5 h and 14.5 h. FIG. 14(c) shows those gels exposed in the air at room temperature for 57.5 h and 56.5 h. FIG. 14(d) shows those gels exposed in the air at room temperature for 221.5 h and 220.5 h.

DETAILED DESCRIPTION OF PARTICULAR EMBODIMENTS

Definitions

Figure 1:
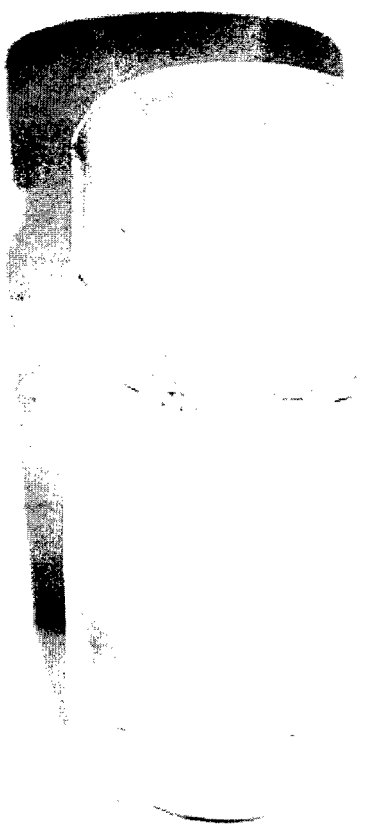
FIG. 1 shows a Goil (ginger flower oil) gel of Sample D.

The following definitions are provided for the purpose of understanding the present subject matter and for constructing the appended patent claims.

It is noted that, as used in this specification and the appended claims, the singular forms "a," "an" and "the" include plural references unless the context clearly dictates otherwise.

The term "gel composition" used in this specification and the appended claims may include a composition that will become viscous with time and turn to a gel within a certain time for use in air fresheners or disinfectors, as well as a composition that is already in the form of gel for air fresheners or disinfectors. Accordingly, the term "a composition for air freshening or disinfecting gel" can be understood as referring to a gel composition for air freshening or disinfecting used herein.

The term "gaseous disinfectant" used herein includes gas disinfectant itself, as well as a disinfectant that can generate gas disinfectant with a chemical/electronic reaction.

The term "silica sol solution" used herein may include the reaction mixture of a silicon alkoxide and an aqueous solution that can contain water and an acid or base catalyst.

The term "fragrance" used herein may include a mixture of multiple fragrant compounds, as well as a single fragrant compound.

Unless defined otherwise all technical and scientific terms used herein have the same meaning as commonly understood to one of ordinary skill in the art to which the presently described subject matter pertains.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques Gel Composition The structure/framework of the gel is made from an inorganic silica network, which is formed from a silica sol solution. The silica sol solution used herein can be prepared by hydrolyzing a silicon alkoxide with water, or it can be a colloidal silica suspension. Further condensation results in the growth, aggregation and inter-linking of the silica sols, which expands to and solidify the entire solution after a certain period of time.

The silicon alkoxide used in the present subject matter may be prepared by a method available in the art or is commercially available. Non-limiting examples of the silicon alkoxide include tetraethyl orthosilicate (TEOS), tetramethyl orthosilicate (TMOS) and tetrapropyl orthosilicate (TPOS), of which TEOS is preferred in use in consideration of its material cost and reactivity. Silicon alkoxide reacts with water (hydrolysis) and transform to silicon hydroxide. Silicon hydroxide further reacts with each other or unhydrolyzed silicon alkoxide and forms a 3-dimensional silica network in the liquid medium, known as condensation while releasing water and/or alcohol molecules at the same time. Hydrolysis and condensation are promoted in the presence of acids and bases. The liquid medium is water, alcohols, other water-soluble solvents and the like. Under proper control, this inorganic silica matrix is a transparent freestanding gel, immobilizing the liquid medium inside.

The colloidal silica suspension used for the gel may be prepared using a method known in the art (see, e.g., U.S. Pat. Nos. 4,927,750 and 6,015,843) or can be commercially obtained. Non-limiting examples of the colloidal silica suspension include Ludox AS-40® from Aldrich (40 wt % suspension in $H_2O$), Ludox AS-30® from Aldrich (30 wt % suspension in $H_2O$) and Ludox TM-40® from Aldrich (40 wt % suspension in $H_2O$), of which Ludox AS-40® is preferred.

An acid or base promotes hydrolysis and condensation of the silicon alkoxide. Any acid or base that can be used as a catalyst for hydrolysis of the silicon alkoxide may be used for the gel composition according to the present subject matter. Non-limiting examples of the acid include hydrochloric acid, nitric acid, citric acid, and the like. Non-limiting examples of the base include ammonium hydroxide, sodium hydroxide, potassium hydroxide, colloidal silica suspension stabilized by alkaline counterion, and the like.

Hydrolysis and condensation can be accelerated also at increased temperature. Accordingly, in an embodiment of the present subject matter, the silica sol solution may be prepared at a temperature of 30 to 50° C. for 1 to 5 hours. Elevated temperature above 50° C. and prolonged time may result in a too viscous silica sol solution or even a gelling solution, which is not desired in the subsequent processing.

A volatile fragrance and/or gaseous disinfectant and/or other volatile components, such as, deodorizers, essential oils, volatile insect repellents and combinations thereof may be incorporated into the gel. The volatile components may also include fragrance raw materials, deodorants, odor counteractants, volatile disinfectants and combinations thereof.

The volatile fragrance and/or other volatile components may be present in the gel composition in an amount of 0 to 85 vol %, preferably 50 to 70 vol %, or more preferably 8 to 35 vol %. In particular, the other volatile components may be present in an amount from 0 to 10 vol %. The gaseous disinfectant may be present in an amount of 0 to 8000 ppm, preferably 800 to 2000 ppm. In all cases, the gel composition comprises at least one of the volatile fragrance and the gaseous disinfectant.

Any volatile fragrance that can be used for air fresheners may be used in the present subject matter. Non-limiting examples of the fragrance are described in, for example, S. Arctander, Perfume and Flavor Materials, Vols. I and II, Monclair, N,N., 1969; Selbstverlag or K. Bauer, D. Garbe and H. Surburg, Common Fragrances and Flavor Materials, 3.sup.rd Ed., Wiley-VCH, WEinheim, 1997. Examples of the fragrance are also described in U.S. Pat. No. 7,235,261. In an embodiment, the gel composition according to the present subject matter contains ginger flower oil (Goil), eucalyptus oil (Eoil), pine tree oil (Poil), tea tree oil (Toil), lemon oil (Loil), or a combination of two or more thereof as a fragrance.

The gaseous disinfectant is generated in the gel composition from a reactant. Non-limiting examples of the gas disinfectants include sulfur dioxide, glyoxal, iodine, chlorine, malondialdehyde and ammonia. In an embodiment, the gel composition according to the present subject matter uses sodium chlorite as the reactant and generates chlorine dioxide ($ClO_2$) as gas disinfectant.

The water-soluble (or water-miscible) solvent is miscible with an aqueous silica sol solution and oily volatile components, mainly the fragrance and in-situ generated disinfectant in the gel composition. Its presence in the gel composition prevents oil-water phase separation, which is often insufficiently solved by microemulsions in the prior art. Non-limiting examples of the water-soluble solvent include propylene glycol, dipropylene glycol, dipropylene glycol methyl ether, isopropylmyristate, diethyl phthalate, glyceryl triacetate, 3-methoxy-3-methyl-1-butanol, benzyl benzoate, PEG 400, glycerol, ethylene glycol, benzyl alcohol, ethanol, isopropanol, and the like. In an embodiment, the gel composition comprises a single water-soluble solvent or a combination of two or more water-soluble solvents.

Figure 6:
FIG. 6 shows Goil gel with a leaf suspended inside.
Figure 7:
FIG. 7 shows Goil gel with a "lucky star" (plastic decoration) suspended inside.
Figure 8:
FIG. 8 shows Goil gel with a statue (plastic decoration) suspended inside.
Figure 9:
FIGS. 9(a) to 9(d) show Eoil (eucalyptus oil) with different colors.
Figure 9:
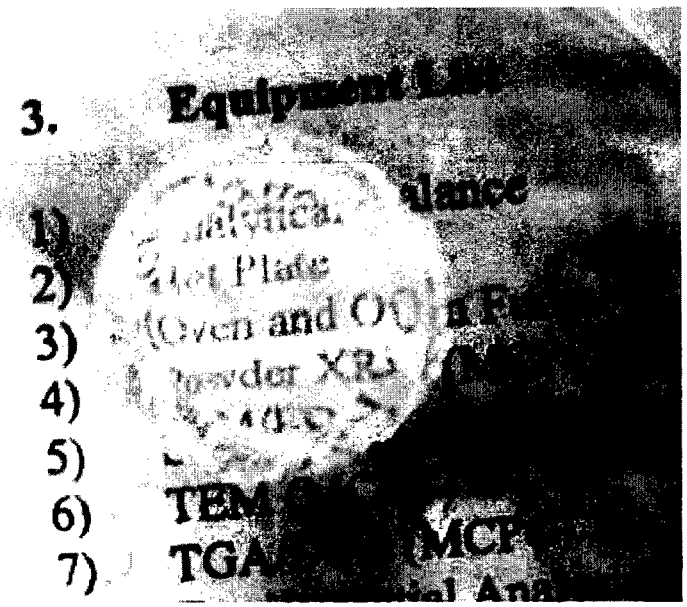
Figure 9:
Figure 9:
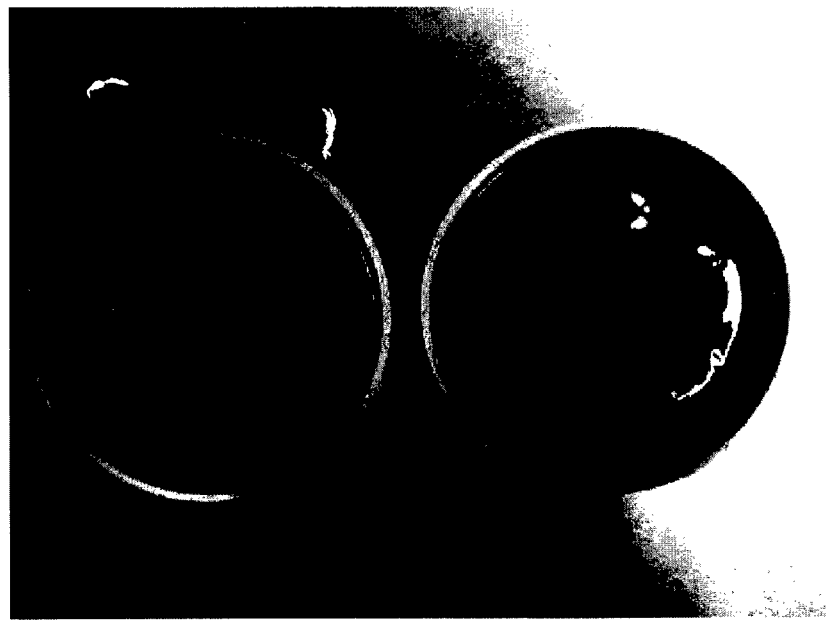

Other additives may be added to achieve visual decorative effects of the gel product. In an embodiment, a dye may be added to the gel formulation with fragrance to prepare colored fragrance gels. In another embodiment, a solid material, such as, a botanical or plastic decoration may be added to give a pleasant impression to the customers. FIG. 6 shows a leaf suspended in Goil gel for decoration purposes. FIG. 7 shows a "lucky star" (plastic decoration) suspended in Goil gel for decoration purposes. FIG. 8 shows a statue (plastic decoration) suspended in Goil gel for decoration purposes.

A preservative or microbiocide may be added to the gel composition to prevent a potential growth of microorganisms or mold causing the gel to develop a sour or unpleasant odor.

The gel produced from the composition is compatible with common glass and plastics. It may be packaged in a transparent glass container or a transparent plastic container in proper shape. The fragrance solution is simply poured into the container and uniformly gelled thereafter at ambient conditions. There is no limitation to the size or shape of the container.

The gel releases fragrance at a steady rate (controlled release) in one month or over several months. The release of the fragrance may be controlled by adjusting the container opening. The in-situ generated gas disinfectant is released by diffusion within the silica gel matrix.

The fragrance gel is storage-stable for several months under sealed conditions. The gel is elastic with resistance of more than 25% deformation under force. The gel composition possesses a suitably low toxicity and low flammability for its intended use in a household or other closed area.

Preparation of the Gel Composition

To prepare a composition of air freshener or disinfector gel, a silicon alkoxide is mixed with water or an acid aqueous solution in a container, and the mixture is strongly blended for about 10 to 30 minutes until a homogeneous, clear solution is obtained. To accelerate hydrolysis of the silicon alkoxide, the solution may be heated in a water bath at 30 to 50° C. for 1 to 5 hours and then cooled to ambient temperature, to obtain a silica sol solution. Since the preparation is performed below the temperature of 50° C., this preparation method is easier and requires less energy consumption and low cost.

The silica sol solution obtained is mixed with a water-soluble solvent(s) with stirring for about 5 to 15 minutes until a homogeneous, clear solution is obtained. A fragrance and other volatile components are then added to the mixture with vigorous stirring for about 5 to 20 minutes to obtain a homogeneous, clear solution. Subsequently, a base aqueous solution is added with vigorous stirring and a homogenous, clear solution is obtained, typically in 10 to 30 minutes. A fragrance solution is thereby obtained.

The fragrance solution is poured into a transparent container and sealed against loss of volatile components upon evaporation. The fragrance solution becomes more and more viscous with time and eventually turns to a transparent fragrance gel in the container.

To prepare a fragrance gel with botanicals or plastic decorations inside, the container is first partially-filled, about half way, with the fragrance solution. After the passage of an amount of time sufficient to develop a required viscosity to support the decoration, a botanical or plastic decoration is added and subsequently the container is filled with the fragrance solution to the desired level. The container should be filled to about one third to three fourths full depending on the desired position of the botanicals or plastic decorations in the container. The time required for the gel to develop sufficient viscosity to support the decorations on its surface will depend on the specific gravity of the decorations relative to that of the gel. The botanicals, if necessary, may be pre-treated by bleaching, freeze-drying, coating or the like before they are added to the gel composition.

Any packaging container of reasonable dimension can be employed for the gel preparation consistent with commercial custom. As described above, however, the container preferably is transparent to allow a viewer to perceive the texture and structure of the gel and a solid suspended therein. Glass containers are preferred although other transparent container materials may also be used to achieve the desired result.

In preparing a disinfectant gel, an acid catalyzes the condensation process of the colloidal silica suspension (e.g., Ludox AS-40®) to form the gel framework and reacts with a salt, such as, sodium chlorite dissolved in the colloidal silica suspension, and generates a gaseous disinfectant, such as chlorine dioxide. The gaseous disinfectant may be generated by a chemical or electrolytic process. For the electrolytic process, a container with a proper device, such as a container equipped with two electrodes, may be used. If necessary, additives such as stabilizers may be included in the gel composition.

Gel Clarity

Gel clarity is determined quantitatively by measuring the visible light transmittance of the gel product prepared according to the method described above. Specifically, i) a plastic disposable cuvette (1 cm×1 cm×4 cm) is filled with a fragrance solution and sealed with parafilm; and ii) after the fragrance solution is gelled, the cuvette is placed in the chamber of a UV/VIS Spectrophotometer (Ultrospec/ 4300pro) and visible light transmittance is recorded from 430 nm to 800 nm. An empty cuvette is used as the reference sample for the measurement.

Figure 2:
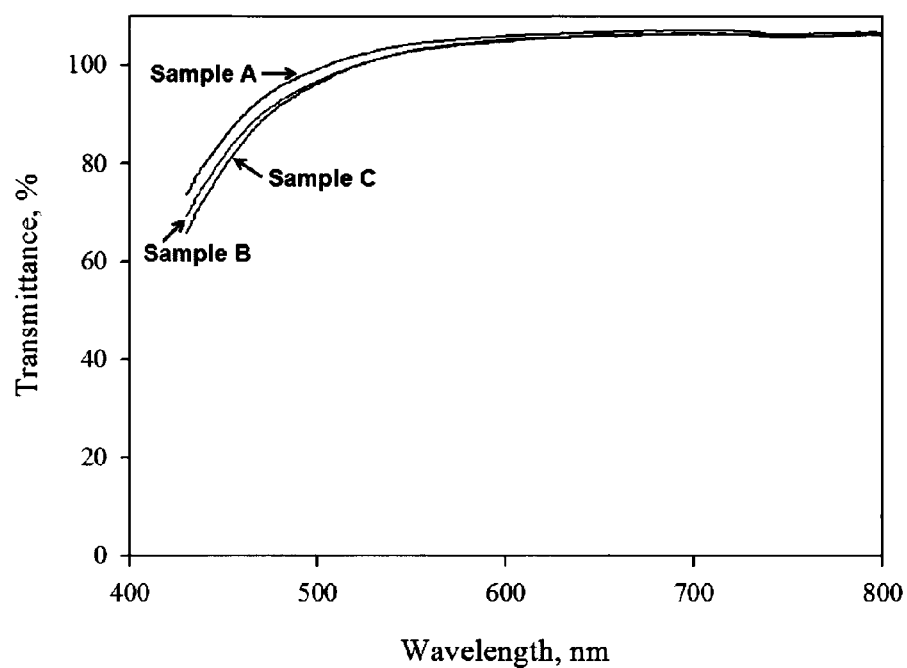
FIG. 2 shows the effects of Goil and TEOS loadings on gel clarity.
Figure 3:
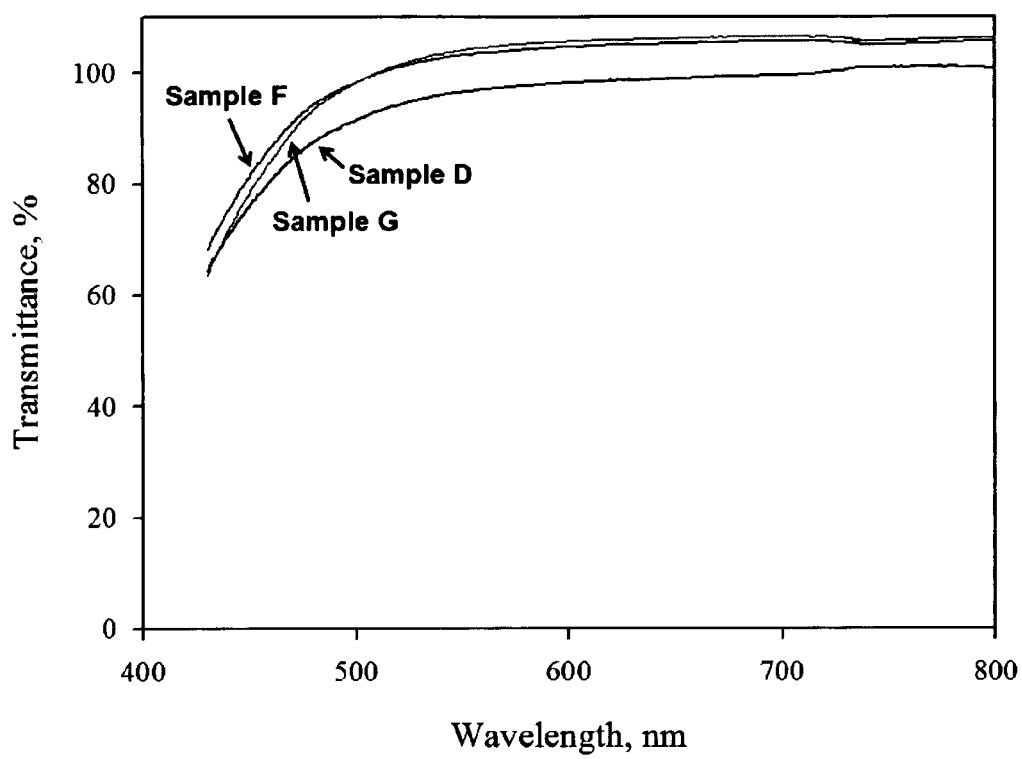
FIG. 3 shows the effect of water-soluble solvents on gel clarity.
Figure 13:
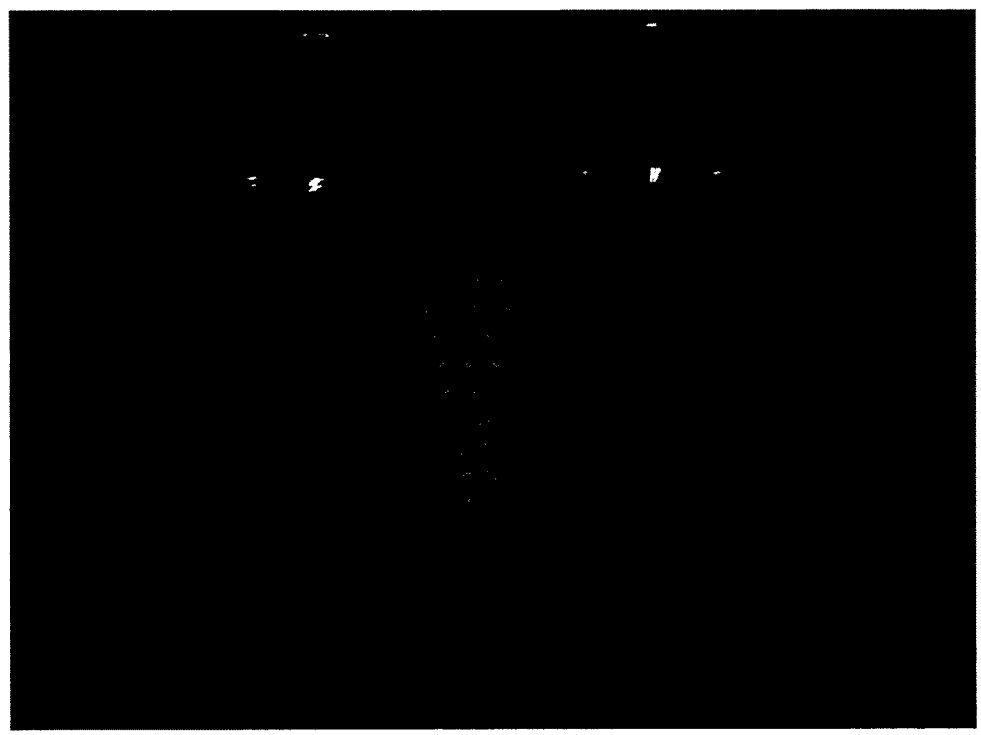
FIG. 13 shows $ClO_2$ gels of Sample Z1 (Left) and Sample Z2 (Right) as-synthesized.
Figure 14:
FIGS. 14(a) to 14(d) show $ClO_2$ gels of Sample Z3 (Left) and Sample Z4 (Right) exposed in the air at room temperature for different time.
Figure 14:
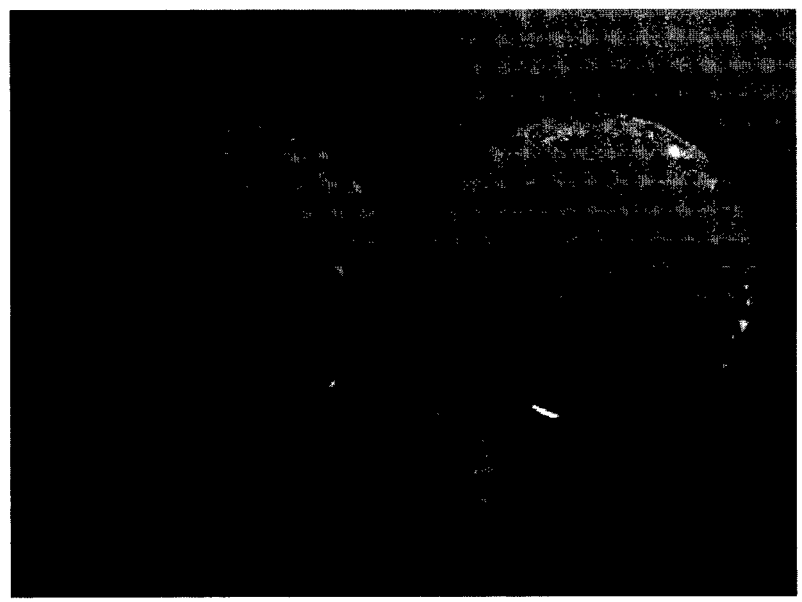
Figure 14C:
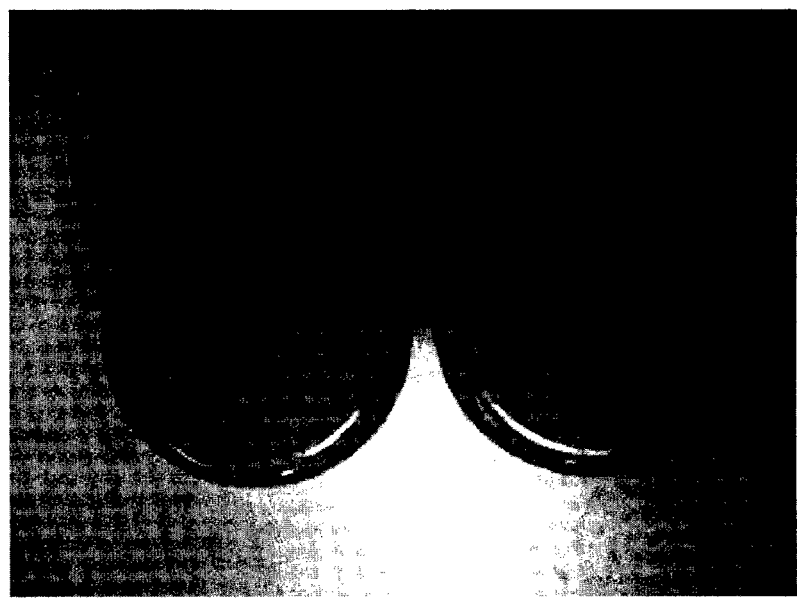
Figure 14:
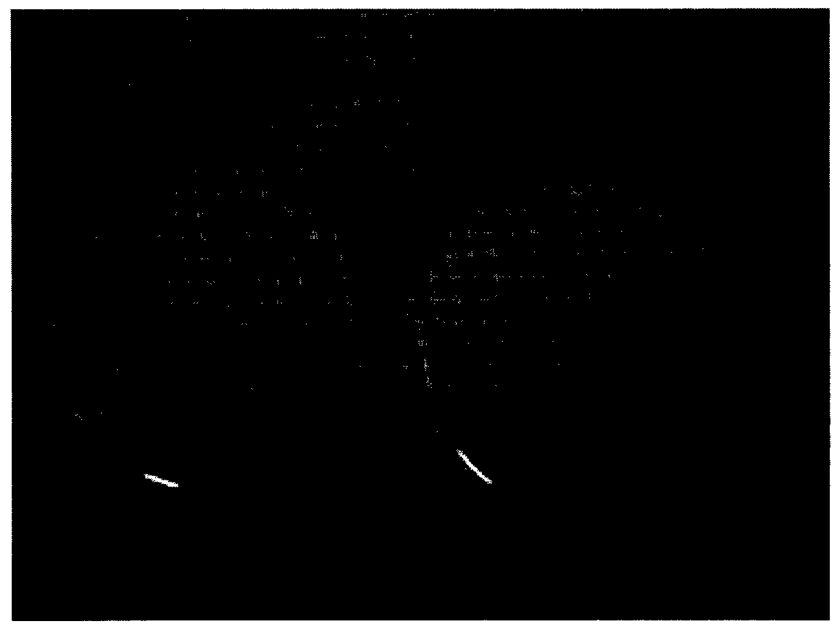
Figure 16:
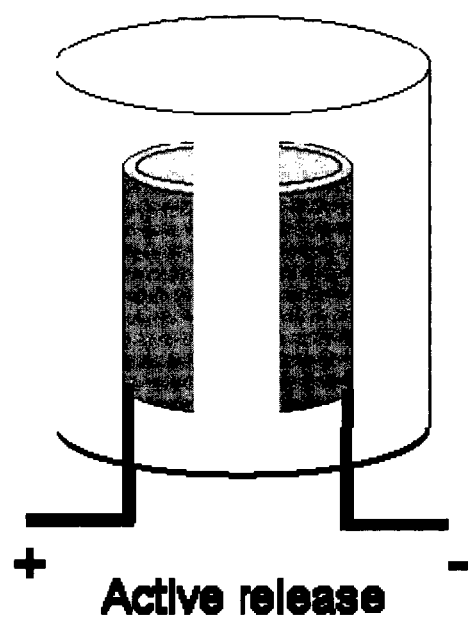
FIG. 16 shows a schematic of $ClO_2$ disinfectant gel with embedded electrode for on-demand generation of the disinfectant

FIG. 1 shows the photo of a typical Goil gel (Sample D of Example 4). It is transparent and free from visual inhomogeneity. The yellow appearance results from the color of the fragrance used. FIG. 2 illustrates the effects of Goil and TEOS loadings on gel clarity. The lower transmittance below 500 nm results from the absorption of Goil in this range. Visible light easily penetrates the gel body, and there is no effect by Goil and TEOS loadings. FIG. 3 demonstrates the effect of water-soluble solvents on gel clarity. All the gels are quite transparent, with no or little difference caused by the solvent used. FIG. 13 shows as-synthesized $ClO_2$ gels with low $ClO_2$ content. They remain in initial morphology and don't show visible bubbles during release in air at room temperature. FIGS. 14(a) to 14(d) show $ClO_2$ gels exposed in air at room temperature for different times. Many pores appear within the gels after several hours, which can indicate release of much $ClO_2$. The color changes from yellow to colorless after releasing for ca. 9 days. FIG. 16 shows a schematic of $ClO_2$ disinfectant gel with embedded electrode for on-demand generation of the disinfectant.

Gel Strength

To determine gel strength, i) a cylindrical gel sample is prepared in a graduated plastic syringe, which has a volume of 4 ml and a diameter of 2 cm; ii) the gel sample is removed from the plastic syringe and placed on the flat test plate of a tensile/compression test module (INSTRON 5567 Tensile/ Compression Tester); and iii) the break strength of the gel is measured as the force (in grams) required to fracture the top surface of the gel using a crosshead speed of 1 mm/sec. The elasticity is calculated by the ratio of the height at which the gel starts to crack to the original height of the gel.

Weight Loss in Use

To determine weight loss of the gel in use, i) 4-ml of a gel sample is made in a 10-ml glass beaker with a diameter of about 2 cm; ii) The beaker is located in a well-ventilated place, for example, an exhaust hood; and iii) sample weight loss (% weight loss) is monitored at room temperature (about 20 to 25° C.).

Figure 4:
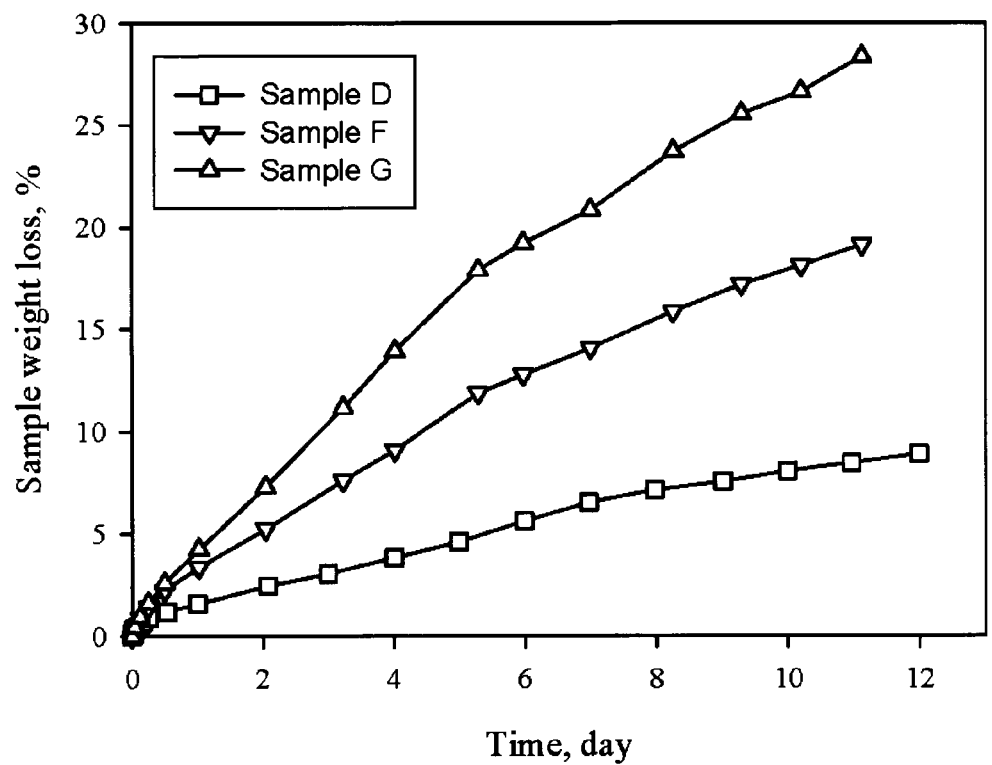
FIG. 4 shows the effect of water-soluble solvents on gel weight loss during use.
Figure 5:
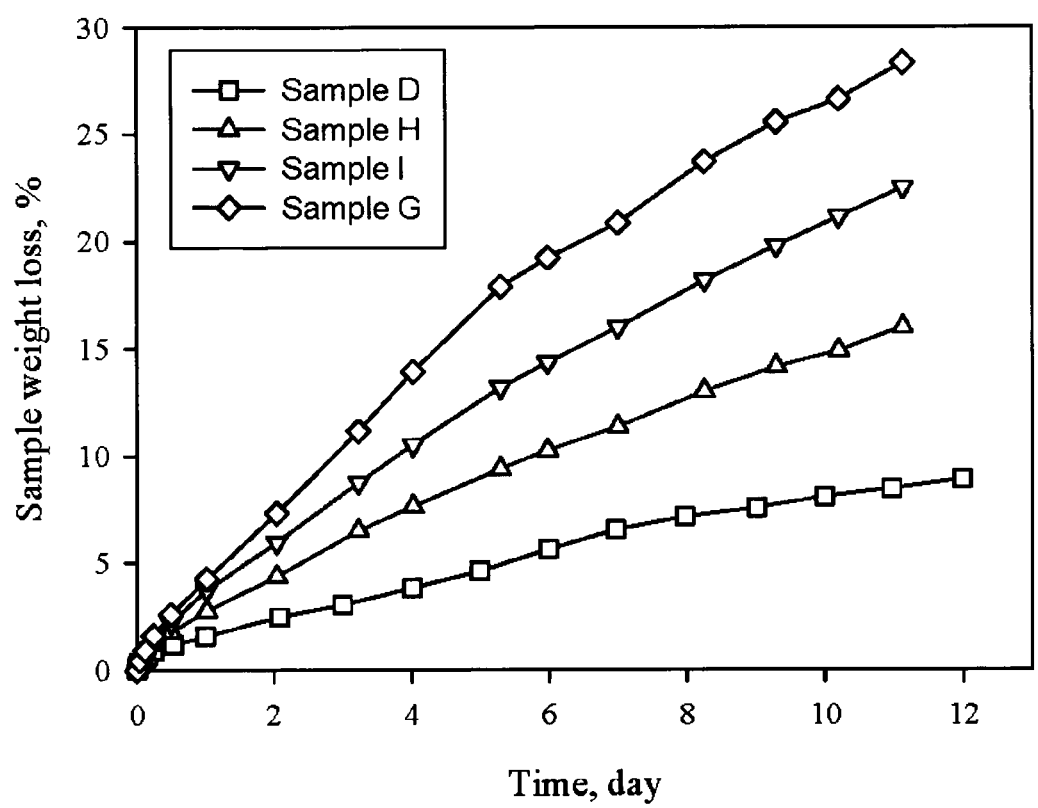
FIG. 5 shows the effect of a combination of water-soluble solvents (dipropylene glycol and 3-methoxy-3-methyl-1-butanol) on gel weight loss during use.
Figure 10:
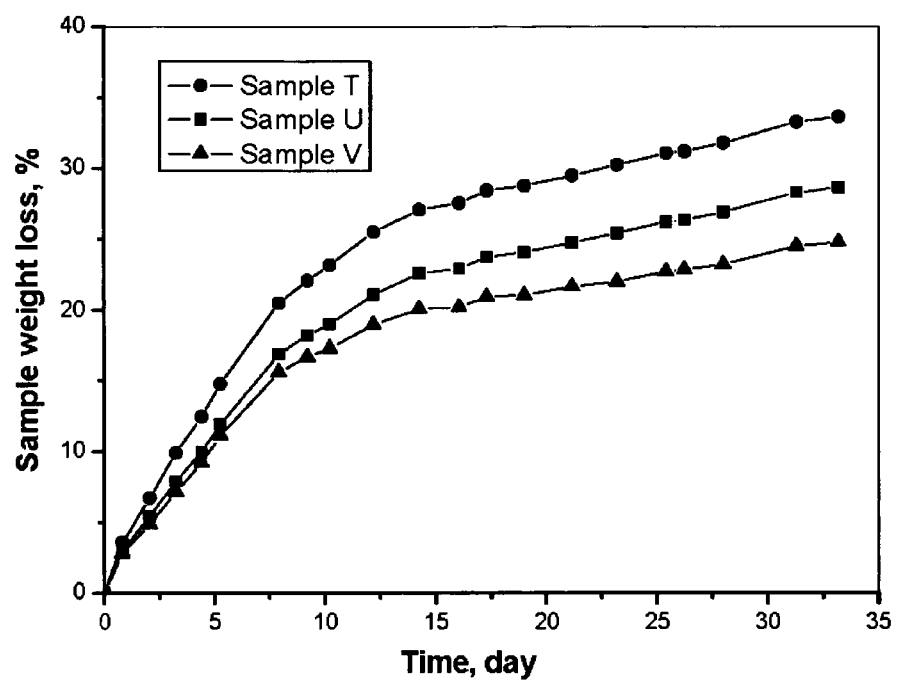
FIG. 10 shows the releasing curves of different Eoil gels exposed in the air at room temperature.
Figure 11:
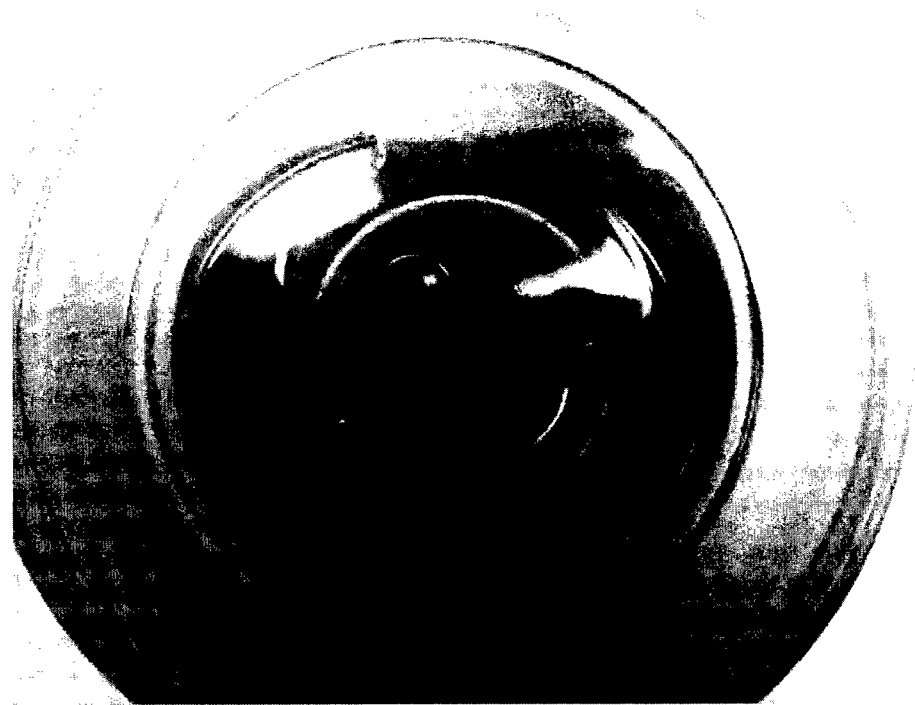
FIG. 11 shows Eoil gel (large-scaled Sample V containing food pigment) stably stored in a sealed box over three months.
Figure 12:
FIG. 12 shows Poil (pine tree oil) gel (250 ppm acid green) and Toil (tea tree oil) gel (50 ppm acid green).

FIG. 4 shows the effects of water-soluble solvent on sample weight loss during use. Weight loss is consistent in about 12 days, and increases with solvent volatility. FIG. 5 shows that the sample weight loss may be moderated using a combination of water-soluble solvents with different volatility, and a desired evaporation rate can be achieved without modifying the container design. FIG. 10 shows the releasing curves of different gels containing eucalyptus oil (Eoil) exposed in air at room temperature. The weights of Sample T, U and V remain basically constant, which are ca. 66%, 71% and 75% of initial weights after 33-day releasing.

UV-Vis Spectra

To determine UV-Vis spectra of the disinfectant gels prepared according to the method described above, i) $ClO_2$ gel is fixed between two quartz pieces with the diameter of 3 cm; and ii) $ClO_2$ gel and quartz pieces are placed in a UV/VIS Spectrophotometer (Perkin-Elmer Lambda 20) to record its UV-Vis spectra from 190 nm to 1100 nm after different releasing time. Pure silica gel is used as the reference sample for the measurement.

Figure 15:
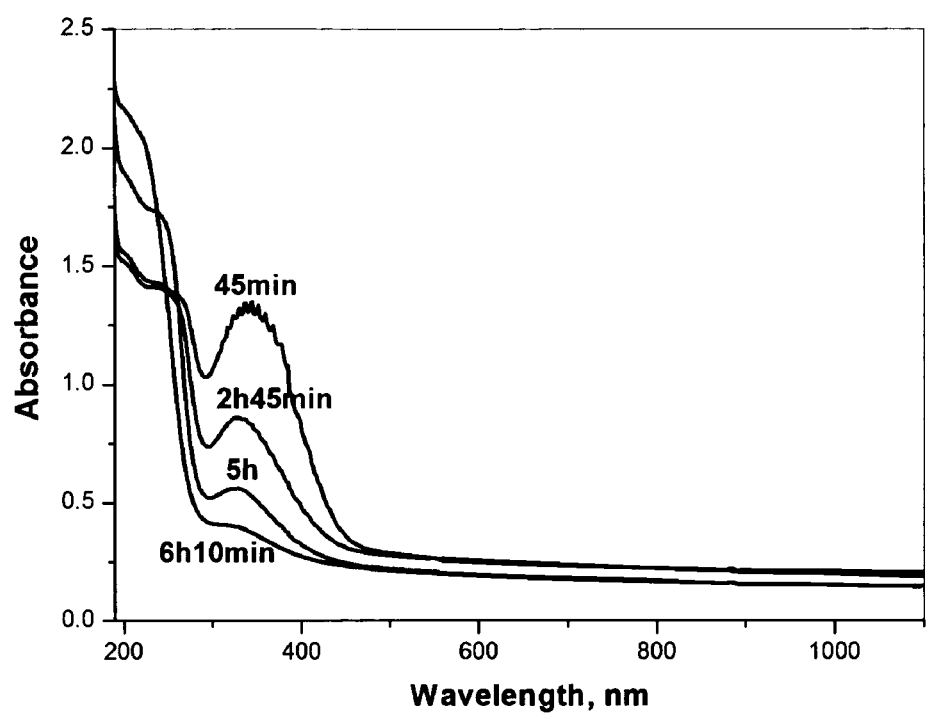
FIG. 15 shows UV-Vis spectra of $ClO_2$ gel exposed in the air at room temperature after different time.

FIG. 15 shows UV-Vis spectra of $ClO_2$ gel exposed in air at room temperature after different times. After releasing for ca. 6 h, the intensity of $ClO_2$ absorption peak is very weak. But the released $ClO_2$ concentration is still above 5 ppm ($ClO_2$ detector). And this high $ClO_2$ concentration can be retained for more than one month.

EXAMPLES

The examples below demonstrate various embodiments of the present subject matter.

Example 1

TEOS-5-DPG-Goil-70

Sample A, TEOS: 5 Vol %, Solvent: DPG, Fragrance: 70 Vol %

5 ml of TEOS is mixed with 1.6 ml of aqueous $HNO_3$ solution (0.14 M) with strong stirring. The mixture is heated at 50° C. for 3 hours and then cooled to room temperature. 21.9 ml of dipropylene glycol, and then 70 ml of a fragrance (ginger flower oil, Goil) is added with strong stirring. A solution containing 0.4 ml of ammonia solution (1.39 M) and 1.2 ml of dipropylene glycol is added with strong stirring. The homogeneous fragrance solution becomes viscous with time and turns to a gel within 2 days.

Example 2

TEOS-5-DPG-Goil-80

Sample B, TEOS: 5 Vol %, Solvent: DPG, Fragrance: 80 Vol %

5 ml of TEOS is mixed with 1.6 ml of aqueous $HNO_3$ solution (0.14 M) with strong stirring. The mixture is heated at 50° C. for 3 hours and then cooled to room temperature. 11.8 ml of dipropylene glycol, and then 80 ml of Goil is added with strong stirring. A solution containing 0.4 ml of ammonia solution (1.39 M) and 1.2 ml of dipropylene glycol is added with strong stirring. The homogeneous fragrance solution becomes viscous and turns to a gel within 1 day.

Example 3

TEOS-10-DPG-Goil-70

Sample C, TEOS: 10 Vol %, Solvent: DPG, Fragrance: 70 Vol %

10 ml of TEOS is mixed with 3.2 ml of aqueous $HNO_3$ solution (0.14 M) with strong stirring. The mixture is heated at 50° C. for 3 hours and then cooled to room temperature. 13.6 ml of dipropylene glycol, and then 70 ml of Goil is added with strong stirring. A solution containing 0.8 ml of ammonia solution (1.39 M) and 2.4 ml of dipropylene glycol is added with strong stirring. The homogeneous fragrance solution becomes viscous and turns to a gel within 1 day.

Example 4

TEOS-10-DPG-Goil-60

Sample D, TEOS: 10 Vol %, Solvent: DPG, Fragrance: 60 Vol %

10 ml of TEOS is mixed with 3.2 ml of aqueous $HNO_3$ solution (0.14 M) with strong stirring. The mixture is heated at 50° C. for 3 hours and then cooled to room temperature. 23.6 ml of dipropylene glycol, and then 60 ml of Goil is added with strong stirring. A solution containing 0.8 ml of ammonia solution (1.39 M) and 2.4 ml of dipropylene glycol is added with strong stirring. The homogeneous fragrance solution becomes viscous and turns to a gel within 1 day.

Example 5

TEOS-10-DPG-Goil-80

Sample E, TEOS: 10 Vol %, Solvent: DPG, Fragrance: 80 Vol %

10 ml of TEOS is mixed with 3.2 ml of aqueous $HNO_3$ solution (0.14 M) with strong stirring. The mixture is heated at 50° C. for 3 hours and then cooled to room temperature. 3.5 ml of dipropylene glycol, and then 80 ml of Goil is added with strong stirring. A solution containing 0.8 ml of ammonia solution (1.39 M) and 2.4 ml of dipropylene glycol is added with strong stirring. The homogeneous fragrance solution becomes viscous and turns to a gel within 1 day.

Example 6

TEOS-10-DPGM-Goil-60

Sample F, TEOS: 10 Vol %, Solvent: DPGM, Fragrance: 60 Vol %

10 ml of TEOS is mixed with 3.2 ml of aqueous $HNO_3$ solution (0.14 M) with strong stirring. The mixture is heated at 50° C. for 3 hours and then cooled to room temperature. 23.6 ml of dipropylene glycol methyl ether, and then 60 ml of Goil is added with strong stirring. A solution containing 0.8 ml of ammonia solution (1.39 M) and 2.4 ml of dipropylene glycol methyl ether is added with strong stirring. The homogeneous fragrance solution becomes viscous and turns to a gel within 1 day.

Example 7

TEOS-10-MMB-Goil-60

Sample G, TEOS: 10 Vol %, Solvent: MMB, Fragrance: 60 Vol %

10 ml of TEOS is mixed with 3.2 ml of aqueous $HNO_3$ solution (0.14 M) with strong stirring. The mixture is heated at 50° C. for 3 hours and then cooled to room temperature. 23.6 ml of 3-methoxy-3-methyl-1-butanol, and then 60 ml of Goil is added with strong stirring. A solution containing 0.8 ml of ammonia solution (1.39 M) and 2.4 ml of 3-methoxy-3-methyl-1-butanol is added with strong stirring. The homogeneous fragrance solution becomes viscous and turns to a gel within 1 day.

Example 8

TEOS-10-DPG-2-MMB-1-Goil-60

Sample H, TEOS: 10 Vol %, Solvent: DPG/MMB 2/1 v/v, Fragrance: 60 Vol %

10 ml of TEOS is mixed with 3.2 ml of aqueous $HNO_3$ solution (0.14 M) with strong stirring. The mixture is heated at 50° C. for 3 hours and then cooled to room temperature. A mixture of 14.9 ml of dipropylene glycol and 8.7 ml of 3-methoxy-3-methyl-1-butanol, and then 60 ml of Goil is added with strong stirring. A solution containing 0.8 ml of ammonia solution (1.39 M) and 2.4 ml of dipropylene glycol is added with strong stirring. The homogeneous fragrance solution becomes viscous and turns to a gel within 1 day.

Example 9

TEOS-10-DPG-1-MMB-2-Goil-60

Sample I, TEOS: 10 Vol %, Solvent: DPG/MMB 1/2 v/v, Fragrance: 60 Vol %

10 ml of TEOS is mixed with 3.2 ml of aqueous $HNO_3$ solution (0.14 M) with strong stirring. The mixture is heated at 50° C. for 3 hours and then cooled to room temperature. A mixture of 6.3 ml of dipropylene glycol and 17.4 ml of 3-methoxy-3-methyl-1-butanol, and then 60 ml of Goil is added with strong stirring. A solution containing 0.8 ml of ammonia solution (1.39 M) and 2.4 ml of dipropylene glycol is added with strong stirring. The homogeneous fragrance solution becomes viscous and turns to a gel within 1 day.

Example 10

TEOS-10-DPG-Goil-60, Sample D

Sample J, Leaf Suspended in DPG Fragrance Gel

A fragrance solution with the gel composition of Example 4 is prepared. A transparent container is half-filled with the fragrance solution. Solution viscosity continues to increase and after several hours the solution is capable of supporting the solid object on it. A leaf is placed in the solution and then another portion of the fragrance solution is added to a desirable level. The gel with leaf inside is formed within 1 day.

Example 11

TEOS-10-DPG-Goil-60, Sample D

Sample K, "Lucky Star" Suspended in DPG Fragrance Gel

A fragrance solution with the gel composition of Example 4 is prepared. A transparent container is half-filled with the fragrance solution. Solution viscosity continues to increase and after several hours the solution is capable of supporting the solid object on it. A "lucky star" (plastic decoration) is placed in the solution and then another portion of the fragrance solution is added to a desirable level. The gel with the "lucky star" inside is formed within 1 day.

Example 12

TEOS-10-DPG-Goil-60, Sample D

Sample L, Statue Suspended in DPG Fragrance Gel

A fragrance solution with the gel composition of Example 4 is prepared. A transparent container is half-filled with the fragrance solution. Solution viscosity continues to increase and after several hours the solution is capable of supporting the solid object on it. A statue (plastic decoration) is placed in the solution and then another portion of the fragrance solution is added to a desirable level. The gel with the statue inside is formed within 1 day.

Example 13

TEOS-32-Water-Eoil-32

Sample M, TEOS: 32 Vol %, Solvent: Water, Fragrance: 32 Vol %

10 ml of TEOS is mixed with 3.2 ml of aqueous $HNO_3$ solution (0.14 M) with strong stirring. The mixture is heated at 50° C. for 3 hours and then cooled to room temperature, followed by the addition of 10 ml of fragrance (eucalyptus oil, Eoil) with strong stirring. Then a solution containing 0.8 ml of ammonia solution (1.39 M) and 7.1 ml of water is added with strong stirring. The homogeneous fragrance solution becomes viscous and turns to a gel within 1 min.

Example 14

TEOS-20-ETH-3-GKY-1-Eoil-20

Sample N, TEOS: 20 Vol %, Solvent: ETH/GLY 3/1 v/v, Fragrance: 20 Vol %

10 ml of TEOS is mixed with 3.2 ml of aqueous $HNO_3$ solution (0.14 M) with strong stirring. The mixture is heated at 50° C. for 3 hours and then cooled to room temperature. Then a solution containing 10 ml of Eoil, 0.8 ml of ammonia solution (1.39 M), 19.5 ml of ethanol and 6.5 ml of glycerol is added with strong stirring. The homogeneous fragrance solution becomes viscous and turns to a gel within 2 min.

Example 15

TEOS-20-ETH-Eoil-20

Sample O, TEOS: 20 Vol %, Solvent: ETH, Fragrance: 20 Vol %

10 ml of TEOS is mixed with 3.2 ml of aqueous $HNO_3$ solution (0.14 M) with strong stirring. The mixture is heated at 50° C. for 3 hours and then cooled to room temperature. Then a solution containing 10 ml of Eoil, 0.8 ml of ammonia solution (1.39 M) and 26 ml of ethanol is added with strong stirring. The homogeneous fragrance solution becomes viscous and turns to a gel after 5 min.

Example 16

TEOS-20-PEG-Eoil-20

Sample P, TEOS: 20 Vol %, Solvent: PEG, Fragrance: 20 Vol %

10 ml of TEOS is mixed with 3.2 ml of aqueous $HNO_3$ solution (0.14 M) with strong stirring. The mixture is heated at 50° C. for 3 hours and then cooled to room temperature, followed by the addition of 10 ml of Eoil with strong stirring. Then a solution containing 0.8 ml of ammonia solution (1.39 M) and 26 ml of PEG 400 is added with strong stirring. The homogeneous fragrance solution becomes viscous and turns to a gel after 5 min.

Example 17

TEOS-20-ETG-Eoil-20

Sample Q, TEOS: 20 Vol %, Solvent: ETG, Fragrance: 20 Vol %

10 ml of TEOS is mixed with 3.2 ml of aqueous $HNO_3$ solution (0.14 M) with strong stirring. The mixture is heated at 50° C. for 3 hours and then cooled to room temperature, followed by the addition of 10 ml of Eoil with strong stirring. Then a solution containing 0.8 ml of ammonia solution (1.39 M) and 26 ml of ethylene glycol is added with strong stirring. The homogeneous fragrance solution becomes viscous and turns to a gel within 7 min.

Example 18

TEOS-38-DPG-Eoil-13-AS

Sample R, TEOS: 38 Vol %, Solvent: DPG, Fragrance: 13 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 3.3 ml of Eoil with strong stirring. Then 6.6 ml of dipropylene glycol and 3.3 ml of Ludox AS-40 containing dyes such as acid green or food pigment are added sequentially with strong stirring. The homogeneous colored fragrance solution becomes viscous and turns to a gel within 10 h.

Example 19

TEOS-43-DPG-Eoil-Loil-14-AS

Sample S, TEOS: 43 Vol %, Solvent: DPG, Fragrance: 14 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 3.3 ml of fragrance (1:1 Eoil and lemon oil (Loil)) with strong stirring. Then 3.3 ml of dipropylene glycol and 3.3 ml of Ludox AS-40 containing dyes such as acid green or food pigment are added sequentially with strong stirring. The homogeneous colored fragrance solution becomes viscous and turns to a gel after 24 h.

Example 20

TEOS-34-DPG-Eoil-11-AS

Sample T, TEOS: 34 Vol %, Solvent: DPG, Fragrance: 11 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 3.3 ml of Eoil with strong stirring. Then 10 ml of dipropylene glycol and 3.3 ml of solution containing Ludox AS-40, water and dyes such as acid green or food pigment are added sequentially with strong stirring. The homogeneous colored fragrance solution becomes viscous and turns to a gel after 40 h at 50° C.

Example 21

TEOS-30-DPG-Eoil-10-AS

Sample U, TEOS: 30 Vol %, Solvent: DPG, Fragrance: 10 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 3.3 ml of Eoil with strong stirring. Then 13 ml of dipropylene glycol and 3.3 ml of solution containing Ludox AS-40, water and dyes such as acid green or food pigment are added sequentially with strong stirring. The homogeneous colored fragrance solution becomes viscous and turns to a gel after 60 h at 50° C.

Example 22

TEOS-32-DPG-Eoil-5-AS

Sample V, TEOS: 32 Vol %, Solvent: DPG, Fragrance: 5 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 1.7 ml of Eoil with strong stirring. Then 13 ml of dipropylene glycol and 3.3 ml of solution containing Ludox AS-40, water and dyes such as acid green or food pigment are added sequentially with strong stirring. The homogeneous colored fragrance solution becomes viscous and turns to a gel after 72 h at 50° C.

Example 23

TEOS-32-DPG-Poil-5-AS

Sample W, TEOS: 32 Vol %, Solvent: DPG, Fragrance: 5 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 1.7 ml of fragrance (pine tree oil, Poil) with strong stirring. Then 13 ml of dipropylene glycol and 3.3 ml of solution containing Ludox AS-40, water and dyes such as acid green or food pigment are added sequentially with strong stirring. The homogeneous colored fragrance solution becomes viscous and turns to a gel after 72 h at 50° C.

Example 24

TEOS-32-DPG-Toil-5-AS

Sample X, TEOS: 32 Vol %, Solvent: DPG, Fragrance: 5 Vol %, Ludox AS-40 as Catalyst 10 ml of TEOS is mixed with 3.2 ml of aqueous $HNO_3$ solution (0.14 M) with strong stirring. The mixture is heated at 50° C. for 3 hours and then cooled to room temperature, followed by the addition of 1.7 ml of fragrance (tea tree oil, Toil) with strong stirring. Then 13 ml of dipropylene glycol and 3.3 ml of solution containing Ludox AS-40, water and dyes such as acid green or food pigment are added sequentially with strong stirring. The homogeneous colored fragrance solution becomes viscous and turns to a gel after 72 h at 50° C.

Example 25

LUDOX-50-$ClO_2$-0

Sample Y, Ludox AS-40: 50 Vol %, Disinfectant: 0 ppm 5 ml of hydrogen chloride (37%) is added drop by drop into 5 ml of Ludox AS-40 under vigorous stirring to obtain a homogeneous solution. The homogenous solution becomes viscous and turns to gel in 20 min via condensation process of the colloidal silica under the catalysis of the acid.

Example 26

LUDOX-50-$ClO_2$-800

Sample Z1, Ludox AS-40: 50 Vol %, Disinfectant: 800 ppm 0.013 g sodium chlorite is dissolved into 5 ml of Ludox AS-40 with strong stirring, followed by drop by drop addition of 5 ml of hydrogen chloride (37%). The obtained yellow solution becomes viscous and turns to a gel after 1 h at ambient temperature via condensation process of colloidal silica under the catalysis of acid, and the gel continuously releases disinfectant that is chlorine dioxide generated from the reaction between sodium chlorite and hydrogen chloride.

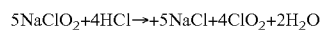

$5NaClO_2 + 4HCl \rightarrow 5NaCl + 4ClO_2 + 2H_2O$

Example 27

LUDOX-50-$ClO_2$-2000

Sample Z2, Ludox AS-40: 50 Vol %, Disinfectant: 2000 ppm 0.034 g sodium chlorite is dissolved into 5 ml of Ludox AS-40 with strong stirring, followed by drop by drop addition of 5 ml of hydrogen chloride (37%). The obtained yellow solution becomes viscous and turns to a gel after 1 h at ambient temperature.

Example 28

LUDOX-50-$ClO_2$-5000

Sample Z3, Ludox AS-40: 50 Vol %, Disinfectant: 5000 ppm 0.084 g sodium chlorite is dissolved into 5 ml of Ludox AS-40 with strong stirring, followed by drop by drop addition of 5 ml of hydrogen chloride (37%). The obtained yellow solution becomes viscous and turns to a gel after 30 min at ambient temperature. The releasing of a large amount of chlorine dioxide results in the formation of macroporous gel.

Example 29

LUDOX-50-ClO$_2$-8000

Sample Z4, Ludox AS-40: 50 Vol %, Disinfectant: 8000 Ppm 0.134 g sodium chlorite is dissolved into 5 ml of Ludox AS-40 with strong stirring, followed by drop by drop addition of 5 ml of hydrogen chloride (37%). The obtained yellow solution becomes viscous and turns to gel after 10 min at ambient temperature. The releasing of a large amount of chlorine dioxide results in the formation of macroporous gel.

Example 30

LUDOX-50-ClO$_2$-8000

Sample ZZ1, Ludox AS-40: 50 Vol %, Disinfectant: 8000 Ppm 0.134 g sodium chlorite is dissolved into 5 ml of Ludox AS-40 with strong stirring, followed by drop by drop addition of 5 ml of hydrogen chloride (37%) to induce gelation. The mixture is poured into a container with two embedded metal electrodes as shown in FIG. 16. Chlorine dioxide was generated by electrolytic process by currents passing across the electrodes. The chlorine dioxide generation can be controlled by the strength of currents and the concentration of salts added in the gel. The chlorine dioxide generated is released from the matrix by diffusion. This allowed metered delivery of the disinfectant on demand.

Experimental Examples

Example A

Sample gels B to G prepared by the methods of Examples 2-7 were tested for the elasticity and strength thereof, and the results are shown in Table 1. Table 1 shows the effects of fragrance, TEOS loadings and water-soluble solvents on gel strength. All the gels are quite elastic, showing more than 25% compression without cracking. The elasticity is higher at lower TEOS loading, while less affected by fragrance loading and solvent used. Soft/medium gel is obtained at a low TEOS loading/high fragrance loading. Rigid gel is obtained at the TEOS loading of 10 vol % and the fragrance loading of 60 vol % and varies with the solvent used.

TABLE 1

The effects of fragrance, TEOS loadings and water-soluble solvents on the strength of Goil gels

| Sample | TEOS, vol % | Goil, vol % | Solvent | Elasticity, % | Strength, gram force |
|---|---|---|---|---|---|
| Sample B | 5 | 80 | DPG | 58 | 35 |
| Sample C | 10 | 70 | DPG | 74 | 188 |
| Sample D | 10 | 60 | DPG | 71 | 170 |
| Sample E | 10 | 80 | DPG | 70 | 69 |
| Sample F | 10 | 60 | DPGM | 68 | 116 |
| Sample G | 10 | 60 | MMB | 71 | 129 |

Note:
1. DPG: dipropylene glycol, DPGM: dipropylene glycol methyl ether, MMB: 3-methoxy-3-methyl-1-butanol
2. Elasticity is represented by the ratio of the height the gel starts to crack to the original height of the gel.
3. Strength is represented by the force in gram to crush the gel.

Example B

Sample gels M to Q prepared by the methods of Examples 13-17 were tested for gelation time, and the results are shown in Table 2. Table 2 shows the effects of preparation parameters on gelation time of the gels containing eucalyptus oil. With the increase of solvent viscosity, gelation time is prolonged gradually.

TABLE 2

The effects of preparation parameters on gelation time of the gels containing *eucalyptus* oil (Eoil gels)

| Sample | TEOS, vol % | Eoil, vol % | Solvent name | Solvent, vol % | Gelation time |
|---|---|---|---|---|---|
| Sample M | 32 | 32 | Water | 23 | <1 min |
| Sample N | 20 | 20 | ETH/GLY (3:1) | 52 | 1~2 min |
| Sample O | 20 | 20 | ETH | 52 | 5 min |
| Sample P | 20 | 20 | PEG | 52 | 5 min |
| Sample Q | 20 | 20 | ETG | 52 | 5~7 min |

Note:
1. ETH: ethanol, GLY: glycerol, PEG: PEG 400, ETG: ethylene glycol.

Example C

Sample gels R to X prepared by the methods of Examples 18-24 were tested for gelation time, and the results are shown in Table 3. Table 3 lists preparation parameters of colored fragrance gels by using Ludox AS-40 as gelation catalyst. Ludox AS-40 is a colloidal silica suspension stabilized by ammonium counterion. It catalyzes condensation process of pre-hydrolyzed silica sol to form gel framework with colloidal silica. For the samples with high solvent/As-40 ratio, gelation time is very long up to months at ambient temperature. Higher temperature, such as 50° C., reduces obviously their gelation time.

TABLE 3

Preparation parameters of colored fragrance gels by using Ludox AS-40 as gelation catalyst

| Sample | TEOS, vol % | Fragrance, vol % | Ludox AS-40, vol % | Solvent, vol % | Gelation time |
|---|---|---|---|---|---|
| Sample R | 38 | Eoil, 13 | 13 | DPG, 25 | <10 h |
| Sample S | 43 | Eoil/Loil, 14 | 14 | DPG, 14 | 24 h |
| Sample T | 34 | Eoil, 11 | 6 | DPG, 33 | 40 h at 50° C. |
| Sample U | 30 | Eoil, 10 | 5 | DPG, 40 | 60 h at 50° C. |
| Sample V | 32 | Eoil, 5 | 5 | DPG, 42 | 72 h at 50° C. |
| Sample W | 32 | Poil, 5 | 5 | DPG, 42 | 72 h at 50° C. |
| Sample X | 32 | Toil, 5 | 5 | DPG, 42 | 72 h at 50° C. |

Note:
1. Loil: lemon oil. Poil: pine tree oil. Toil: tea tree oil.
2. Dyes such as acid green or food pigment are added into mixed sol to prepare colored fragrance gels

Example D

Samples Y to Z4 prepared by the methods of Examples 25-19 were tested for gelation time, and the results are shown in Table 4. Table 4 lists preparation parameters of the gels containing the disinfectant of chlorine dioxide. The gels with different ClO$_2$ contents are prepared by adjusting the content of sodium chlorite.

TABLE 4

Preparation parameters of the gels contained disinfectant chlorine dioxide (ClO$_2$ gels)

| Sample | Ludox AS-40, vol % | Generated ClO$_2$ ppm | Gelation time |
|---|---|---|---|
| Sample Y | 50 | 0 | 20 min |
| Sample Z1 | 50 | 800 | 1 h |
| Sample Z2 | 50 | 2000 | 1 h |
| Sample Z3 | 50 | 5000 | 30 min |
| Sample Z4 | 50 | 8000 | 10 min |

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

What is claimed is:

1. An air freshening or disinfecting gel composition comprising a mixture of:
   (i) a first component selected from the group consisting of at least one silicon alkoxide, at least one colloidal silica, and a combination thereof; wherein the silicon alkoxide is selected from the group consisting of tetramethyl orthosilicate, tetraethyl orthosilicate, tetrapropyl orthosilicate, and a combination thereof;
   (ii) a second component selected from the group consisting of a volatile component, a gaseous disinfectant, and a combination thereof; wherein the volatile component is selected from the group consisting of fragrances, deodorizers, essential oils, insect repellants, and a combination thereof;
   (iii) water;
   (iv) an acid or base catalyst; and
   (v) a solvent selected from the group consisting of ethylene glycol, propylene glycol, glycerol, dipropylene glycol, polyethylene glycol, dipropylene glycol methyl ether, isopropyl myristate, diethyl phthalate, glyceryl triacetate, benzyl benzoate, 3-methoxy-3-methyl-1-butanol, benzyl alcohol, ethanol, isopropanol, and a combination thereof;
   and wherein the gel composition (a) is transparent having a light transmittance of at least 80% as measured spectrophotometrically at the range of 500-800 nm; (b) releases the volatile component or gaseous disinfectant at a steady rate over a period of at least one month to the surrounding environment; and (c) has an elasticity allowing more than 25% compression without cracking.

2. The gel composition according to claim 1, wherein the first component is present in an amount of 5-50 vol % based on total volume of the gel composition; the volatile component is present in an amount of from more than 0 to 85 vol % based on total volume of the gel composition; the gaseous disinfectant is present in an amount of from more than 0 to 8000 ppm based on total weight of the gel composition; and water is present in an amount of 1-50 vol % based on total volume of the gel composition.

3. The gel composition according to claim 1, wherein the volatile component is present in an amount of 50-70 vol % based on the total volume of the gel composition.

4. The gel composition according to claim 1, wherein the volatile component is present in an amount of 8-35 vol % based on the total volume of the gel composition.

5. The gel composition according to claim 1, wherein the gaseous disinfectant is present in an amount of 800-2000 ppm based on total weight of the gel composition.

6. The gel composition according to claim 1, wherein the gaseous disinfectant is chlorine dioxide.

7. The gel composition according to claim 1, wherein the acid is selected from the group consisting of HNO$_3$, HCl, H$_2$SO$_4$, H$_3$PO$_4$ and citric acid.

8. The gel composition according to claim 1, wherein the base is selected from the group consisting of NH$_4$OH, NaOH, KOH and an alkaline colloidal silica suspension.

9. The gel composition according to claim 1 further comprising a botanical.

10. The gel composition according to claim 1 further comprising a plastic decoration.

11. The gel composition of claim 1, wherein the second component includes at least one fragrance and at least one gaseous disinfectant.

12. The gel composition of claim 1, wherein the acid or base is selected from the group consisting of HNO$_3$, HCl, H$_2$SO$_4$, H$_3$PO$_4$, citric acid, NH$_4$OH, NaOH, KOH and an alkaline colloidal silica suspension.

* * * * *